United States Patent [19]

Brotherton et al.

[11] Patent Number: 5,157,152

[45] Date of Patent: Oct. 20, 1992

[54] PROCESS FOR THE OXIDATION OF A TETRAHYDROPHTHALIC ACID

[75] Inventors: David L. Brotherton; Kwok W. Fung; Kam H. Wong, all of Easley, S.C.

[73] Assignee: Ortec, Inc., Easley, S.C.

[21] Appl. No.: 727,578

[22] Filed: Jul. 9, 1991

Related U.S. Application Data

[63] Continuation-in-part of Ser. No. 415,890, Oct. 2, 1990, Pat. No. 5,047,587.

[51] Int. Cl.$^5$ .............................................. C07C 51/285
[52] U.S. Cl. .................................. 562/508; 562/418; 562/421; 562/525
[58] Field of Search ................. 562/418, 421, 508, 525

[56] References Cited

U.S. PATENT DOCUMENTS

| | | | |
|---|---|---|---|
| 2,203,628 | 6/1940 | Hopff et al. | 562/509 |
| 3,284,492 | 11/1966 | Fremery et al. | 562/528 |
| 3,535,367 | 10/1970 | Inoue et al. | 562/508 |
| 3,915,997 | 10/1975 | Ladd | 549/245 |
| 4,305,824 | 12/1981 | Uemura et al. | 210/500.2 |
| 4,331,608 | 5/1982 | Kawamoto et al. | 260/406 |
| 4,391,945 | 5/1983 | Mashio et al. | 524/600 |
| 4,532,079 | 7/1985 | Venturello et al. | 260/413 |
| 4,820,307 | 4/1989 | Welch et al. | 8/120 |
| 4,833,272 | 5/1989 | Nakazawa et al. | 562/523 |

FOREIGN PATENT DOCUMENTS 510638 8/1939 United Kingdom .

OTHER PUBLICATIONS

Venturello et al., *J. Org. Chem.*, vol. 51 (1986), pp. 1599–1601.
Franz et al., *Chem. and Ind.* Feb. 25, 1961, pp. 250–251.
Franz et al., *J. Org. Chem.*, vol. 30 (1965), pp. 1488–1491.

*Primary Examiner*—Jose G. Dees
*Assistant Examiner*—Vera C. Clarke
*Attorney, Agent, or Firm*—Cort Flint

[57] ABSTRACT

A process for oxidation of a tetrahydro compound of the formula

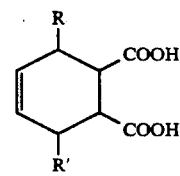

wherein R and R' independently are H, alkyl, aryl or halo, to a glycol of the formula

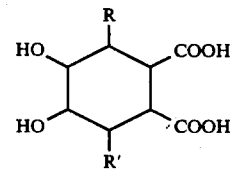

comprises treating the tetrahydro compound with hydrogen peroxide at an elevated temperature under reflux conditions in the absence of a catalyst. The thus-formed glycol can be further oxidized to a butanetetracarboxylic acid of the formula

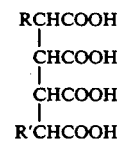

with hydrogen peroxide in the presence of a catalyst selected from the group consisting of a manganese salt, an iron salt, a chromium salt, a cerium salt, a persulfate, a perborate, a silicate, tungstic acid or an ammonium or alkali metal salt or heteropolyacid thereof, or molybdic acid or an ammonium or alkali metal salt or heteropolyacid thereof.

21 Claims, 2 Drawing Sheets

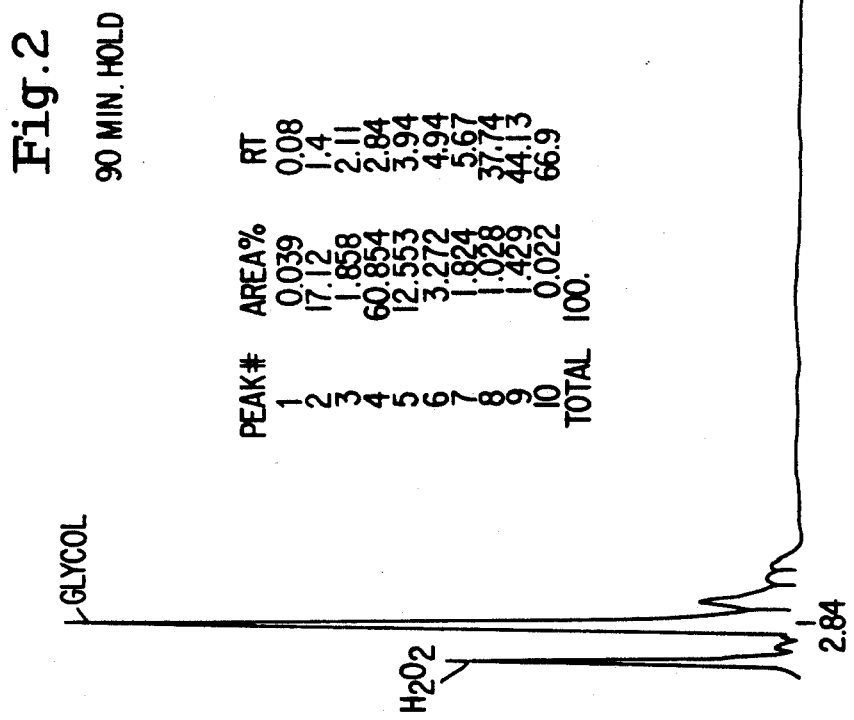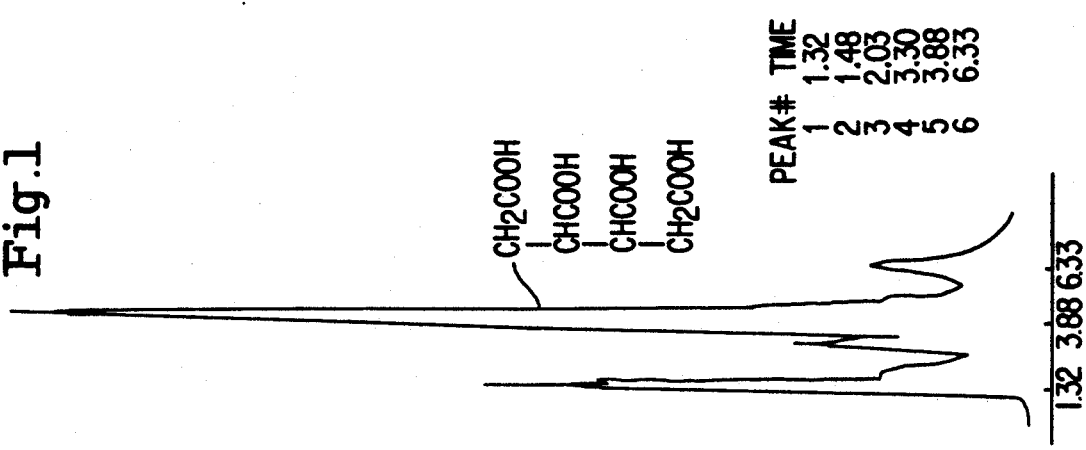

Phosphotungstic Acid
2.5g/3hr.

Na₂WO₄·2H₂O Catalyst
3.0g/3hr.

PROCESS FOR THE OXIDATION OF A TETRAHYDROPHTHALIC ACID

REFERENCE TO RELATED APPLICATION

This is a continuation-in-part of application Ser. No. 07/415,890, filed Oct. 2, 1989, now U.S. Pat. No. 5,047,582.

TECHNICAL FIELD

This invention relates to a process for the non-catalytic oxidation of tetrahydrophthalic acids with hydrogen peroxide to 4,5-dihydroxyhexahydrophthalic acids. Further catalytic oxidation of the intermediate 4,5-dihydroxyhexahydro compounds with hydrogen peroxide yields butane-1,2,3,4-tetracarboxylic acids.

Butanetetracarboxylic acids are used in the preparation of cellulosic reverse osmosis membranes, as proposed by Uemura et al. (U.S. Pat. No. 4,305,824); for chelate resins, as proposed by Mashio et al. (U.S. Pat. No. 4,391,945) and for durable-press finishing of cotton textiles, as proposed by Welch et al. (U.S. Pat. No. 4,820,307). It is, therefore, apparent that improved methods for synthesizing butanetetracarboxylic acids are of interest.

BACKGROUND ART

Nakazawa et al. (U.S. Pat. No. 4,833,272), herein incorporated by reference, have proposed a process for preparing polycarboxylic acids by subjecting a Diels-Alder adduct of maleic anhydride and a diene to oxidation with hydrogen peroxide in the presence of a catalyst selected from tungstic acid, molybdic acid or heteropolyacids thereof.

Venturello et al. (U.S. Pat. No. 4,543,079) have proposed oxidative cleavage of olefins or vicinal dihydroxy compounds by treatment with hydrogen peroxide in a biphasic aqueous liquid/organic liquid, in the presence of a catalyst. Catalysts include tungsten quaternary ammonium, phosphonium, arsonium or stibonium compounds. A mechanism for the reaction is presented by Venturello et al., *J. Org. Chem.*, vol. 51 (1986), pages 1599-1601.

Fremery et al., in U.S. Pat. No. 3,284,492, have proposed preparing carboxylic acids by ozonization of olefinic bonds in an emulsion containing hydrogen peroxide.

Kawamoto et al. (U.S. Pat. No. 4,331,608) have recited a liquid phase catalytic process for co-oxidizing unsaturated compounds, including unsaturated alicyclic compounds, in which oxygen and an aldehyde are present, along with a ruthenium catalyst.

Inoue et al. (U.S. Pat. No. 3,535,367) have recited a process for preparing 4-hydroxycyclohexanecarboxylic acids by treating a cyclohexenecarboxylic acid with sulfuric acid and hydrolyzing a resulting intermediate.

The oxidation of tetrahydrophthalic acid or anhydride to butanetetracarboxylic acid, with nitric acid, generally in the presence of a vanadium catalyst, has been investigated by:

Hopff et al., U.S. Pat. No. 2,203,628; Ladd, U.S. Pat. No. 3,915,997; Johnson, GB Patent 510,638; Franz et al., *Chem. and Ind.*, (London), Feb. 25, 1961, pages 250-251; Franz et al., *J. Org. Chem.*, vol. 30 (1965), pages 1488-1491.

It is an object of this invention to provide a two-step process for the preparation of butanetetracarboxylic acids, in which a tetrahydrophthalic acid is oxidized with aqueous hydrogen peroxide to a corresponding 4,5-dihydroxyhexahydrophthalic compound, which is further oxidized to a butanetetracarboxylic acid with hydrogen peroxide in the presence of a metal-containing catalyst. Advantages of the process include better control over an exothermic process, than heretofore, and production of a cleaner reaction product.

DISCLOSURE OF INVENTION

In one aspect, this invention relates to a process for oxidation of a tetrahydro compound of the formula

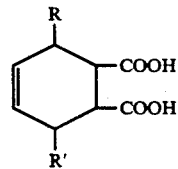

wherein R and R' are independently H, alkyl, aryl or halo, to a glycol of the formula

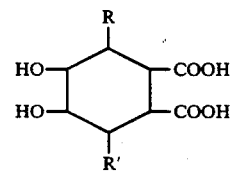

comprising treating the tetrahydro compound with hydrogen peroxide at an elevated temperature under reflux conditions in the absence of a catalyst.

In another aspect, the invention relates to a process for further oxidation of the thus-formed glycol to a butanetetracarboxylic acid of the formula

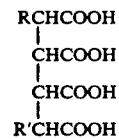

with hydrogen peroxide under reflux conditions in the presence of a catalyst selected from the group consisting of a manganese salt, an iron salt, a chromium salt, a cerium salt, a perborate, a persulfate, a silicate, tungstic acid or an ammonium or alkali metal salt or heteropolyacid thereof, or molybdic acid or an ammonium or alkali metal salt or heteropolyacid thereof.

DETAILED DESCRIPTION

The starting materials used to prepare cyclic vicinal-glycol intermediates of this invention are Diels-Alder adducts of maleic acid, maleic anhydride, or fumaric acid and a 1,3-diene. The diene may be unsubstituted or may be substituted in the 1- and/or 4-positions. The 1- or 4-substituent may be selected from alkyl, aryl or halo substituents, of which methyl, ethyl, butyl, hexyl, 2-ethylhexyl, dodecyl, isostearyl, phenyl, tolyl, chlorophenyl, alpha- or beta-naphthyl, chloro-, bromo- and iodo- are representative. The substituents represented by R and R' are therefore selected from alkyl of 1–18 carbon atoms, mono- or bicyclic- aryl of up to 10 carbon atoms or halo. When the desired product from further oxidation of the intermediate glycol is butanetetracarboxylic acid, the adduct from butadiene-1,3 (R=R'=H) will be employed.

It will be understood that maleic acid, maleic anhydride and fumaric acid include substituted derivatives, such as methylmaleic acid.

The non-catalytic oxidation of a tetrahydrophthalic acid or anhydride is carried out with aqueous hydrogen peroxide at an elevated temperature. When a tetrahydrophthalic anhydride is the starting material, it is preferred to first hydrolyze the anhydride to a corresponding phthalic acid by heating with water at an elevated temperature. Preferably, this hydrolysis will be carried out at a temperature close to boiling, most preferably from about 80° C. to the boiling point of the reaction mixture. It has been found, in the case of highly concentrated aqueous systems, that the boiling point of the mixture can be from about 100° C. to about 115° C. and that the process can advantageously be done at these temperatures. Most preferably, the reaction mixture is heated from about 100° C. to about 110° C.

Even if a tetrahydrophthalic anhydride is not subjected to hydrolysis prior to oxidation to a vicinal glycol, it will be appreciated that hydrolysis to a corresponding diacid would occur under the reaction conditions used.

The oxidation of a tetrahydrophthalic acid/anhydride with hydrogen peroxide is carried out in an aqueous medium in the absence of an organic solvent. Temperatures above about 50° C. are contemplated for the oxidation of a tetrahydrophthalic acid or anhydride to a corresponding glycol. In order to achieve a reasonably fast reaction, it is preferred to carry out this oxidation at 70°-100° C., most preferably at 80°-90° C. It has been found that substantial conversion of tetrahydrophthalic starting material to glycol occurs within 3-4 hours at these temperatures. The time required for conversion of tetrahydrophthalic compound to glycol can be determined by routine procedures, for example, HPLC. Formation of the intermediate glycol is demonstrated by HPLC. The peak corresponding to the intermediate glycol is, for example, the peak at 3.27 min retention time on FIG. 1. The product was also identified by its $^{13}$C NMR spectrum.

It has further been found that the non-catalytic oxidation of a tetrahydrophthalic acid to a 4,5-dihydroxytetrahydrophthalic acid can be done at temperatures above the nominal boiling point of water, more particularly at temperatures from about 100° C. to a maximum temperature, determined by the concentration of reactants in the mixture. The rate of reaction at higher temperatures has been found to be faster, than at lower temperatures. Heating from about 100° C. to about 115° C. is preferred. Most preferably, the mixture is heated from about 100° to about 110° C.

The amount of hydrogen peroxide required for the intermediate conversion is 1-2.6 moles of hydrogen peroxide per mole of olefinic bond in the tetrahydrophthalic starting material. Most preferably, 1.8-2.5 moles of hydrogen peroxide are used per mole of tetrahydrophthalic starting material. It is most preferred to use 1.8-2.5 moles of hydrogen peroxide at lower temperatures and 1.1-1.8 moles of hydrogen peroxide at temperatures near the boiling point.

Although hydrogen peroxide of any concentration can be used, it is preferred to employ a reaction medium containing 5-20% by weight of hydrogen peroxide. This is accomplished by adding concentrated hydrogen peroxide, for example, 50% hydrogen peroxide, to an aqueous medium containing the tetrahydrophthalic starting material. The exact combination of aqueous medium and concentrated hydrogen peroxide can be determined by well-known methods.

It is preferred to carry out the process in an aqueous solvent system. In some instances, however, it is feasible to employ a solvent mixture, including an organic cosolvent. Typical cosolvents are methanol, ethanol, isopropanol, dioxane, tetrahydrofuran, dimethylformamide or the like.

Oxidation of the intermediate glycol is carried out by adding catalyst to the resulting reaction mixture and then adding more hydrogen peroxide and heating.

Catalysts can be selected from among manganese salts, iron salts, chromium salts, cerium salts, perborates, persulfates, silicates, tungstic acid or an ammonium or alkali metal salt or heteropolyacid thereof, or molybdic acid or an ammonium or alkali metal salt or heteropolyacid thereof.

Manganese salts include, but are not limited to the chloride, bromide, iodide, nitrite, sulfate, acetate, benzoate or oxalate as well as salts of higher oxidation states, including potassium permanaganate. Preferably the manganese salt is a salt of Mn(II), of which manganous chloride is particularly preferred.

Iron salts include, but are not limited to, ferrous or ferric chloride, bromide, iodide, nitate, sulfate, oxalate, acetate, etc. Preferably, the iron salt is of Fe(II), of which ferrous sulfate is most preferred.

Tungstic acid means "$WO_3$" or "$H_2WO_4$". A preferred salt catalyst is sodium tungstate, which is represented by the formula $Na_2WO_4$. Usually sodium tungstate is used in the form of a dihydrate.

Chromium salts include water soluble species of various valence states of chromium, of which dichromate species are preferred. A most preferred chromium salt catalyst is potassium dichromate, represented by the formula $K_2Cr_2O_7$.

Cerium salts include those having ammonium functions, particularly cerium (IV) ammonium salts, such as $(NH_4)_2Ce(SO_4)_3.2H_2O$ or $(NH_4)_2Ce(NO_3)_6.4H_2O$. The sulfate salt is a preferred catalyst.

Perborates include species such as $Na_2B_4O_7.H_2O$, $NaBO_3.H_2O$ and $NaBO_2.3H_2O$. A preferred species for the purposes of this invention is $Na_2B_4O_7$.

Persulfates are salts of peroxydisulfuric acid, of which the disodium and diammonium salts are representative. The disodium salt ($Na_2S_2O_8$) is preferred.

Silicates useful as catalysts in the process of this invention include, but are not limited to, potassium metasilicate, potassium tetrasilicate, sodium metasilicate, sodium orthosilicate and sodium tetrasilicate. A preferred catalyst is sodium metasilicate ($Na_2SiO_3$) or its pentahydrate.

A heteropolyacid of tungsten is a polyacid compound obtained from tungstic acid and at least one other oxyacid. Other hetero-atoms in heteropolyacids of tungsten include, P, As, Si, Ti, Co, Fe, B, V, Be, I, Ni, Ga, etc. Heteropolyacids of tungsten therefore include $H_3[PW_{12}O_{40}]$, $H_3[AsW_{12}O_{40}]$, $H_5[BW_{12}O_{40}]$, etc., as disclosed by Nakazawa et al. '272, supra. A preferred heteropoly acid of tungstic acid is phosphotungstic acid.

Molybdic acid corresponds to the formula $MoO_3$ or $H_2MoO_4$. Commonly used "molybic acid" is an ammonium salt, which contains 84-86% of $MoO_3$. Exemplary hetero-atoms in heteropolyacids of molybdenum include P, As, Si, Ge, Ti, Ce, Th, Mn, Ni, Te, I, Co, Cr, Fe, Ga, etc. A particularly preferred molydenum catalyst is the class of compounds known as phosphomolybdic acid, for which the approximate formula is 24 $MoO_3 \cdot P_2O_5 \cdot xH_2O$.

Most preferred catalysts for the process are sodium tungstate and phosphotungstic acid, which give good yields of butanetetracarboxylic acids.

The level of catalyst is generally 0.1-15% by weight of the total charge of intermediate glycol, etc. More preferably, the catalyst level is 0.4-5% by weight.

The amount of hydrogen peroxide used in the catalytic oxidation of an intermediate glycol to a butanetetracarboxylic acid is 3.0-4.5 moles of hydrogen peroxide per mole of glycol. Most preferably, 3.2-3.9 moles are used.

The catalytic oxidation is carried out in the same temperature range as the non-catalytic oxidation of tetrahydrophthalic starting material to glycol. Accordingly, temperatures from about 80° C. to the boiling point of the reaction mixture under ambient pressure are preferred for the oxidation of an intermediate glycol to a butanetetracarboxylic acid. In the case of aqueous reaction mixtures, it has been found that reaction temperatures from about 100° C. to about 115° C. are preferred and most preferred reaction temperatures are from about 100° C. to about 115° C.

It has been found that processes run above the nominal boiling point of water, particularly in the range from about 100° C. to about 115° C., are faster than reactions run at lower temperatures and that the product yield and quality are acceptable. It is accordingly advantageous, from economic considerations, to carry out higher temperature, faster reactions, which permit optimal utilization of production equipment.

It has been found that adding hydrogen peroxide incrementally to the aqueous reaction mixture of glycol and catalyst, gives best results. Hydrogen peroxide is therefore added in 5-20 equal portions at intervals of 15 min-2 h. Hydrogen peroxide can also be added using a metering pump or by dropwise addition to a reaction mixture.

Formation of a typical product, butanetetracarboxylic acid, is shown on FIG. 1, in which butanetetracarboxylic acid corresponds to the peak with a retention time of 3.88 min. The formation of butanetetracarboxylic acid was also demonstrated by comparison of a $^{13}C$ NMR spectrum with that of an authentic sample.

BRIEF DESCRIPTION OF THE DRAWINGS

In FIG. 1 is shown the HPLC chromatogram for the sodium tungstate-catalyzed oxidation of 4,5-dihydroxyhexahydrophthalic acid to butanetetracarboxylic acid as in Example 2.

In FIG. 2 is shown an HPLC chromatogram for the high temperature oxidation of tetrahydrophthalic acid to 4,5-dihydroxytetrahydrophthalic acid.

BEST MODE FOR CARRYING OUT THE INVENTION

Figure 4:
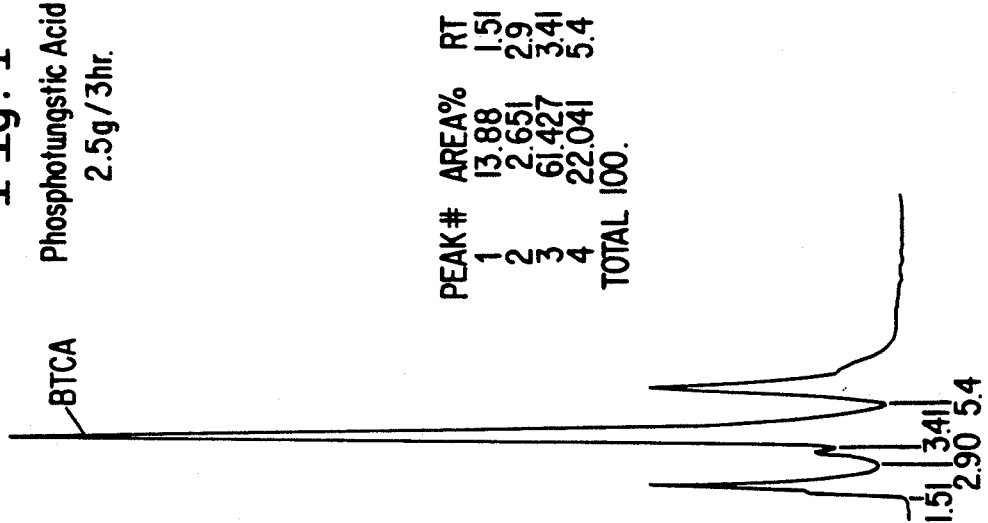
In FIGS. 3 and 4 are shown HPLC chromatograms for the present high temperature process, using sodium tungstate and phosphotungstic acid catalysts, respectively.

In a most preferred embodiment, the starting material is tetrahydrophthalic acid or anhydride (R=R''=H) and the product is butane-1,2,3,4-tetracarboxylic acid.

The non-catalytic step is preferably done at from about 100° C. to about 110° C., using 1.1-1.8 moles of hydrogen peroxide per mole of tetrahydrophthalic starting material.

Most preferred catalysts for the further oxidation of intermediate glycol are sodium tungstate and phosphotungstic acid. Most preferably, hydrogen peroxide is added incrementally or continuously to a reaction mixture containing glycol and catalyst, further oxidation is carried out from about 100° C. to about 110° C., and 3.2-3.9 moles of hydrogen peroxide are used per mole of intermediate glycol.

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperatures are set forth uncorrected in degrees Celsius. Unless otherwise indicated, all parts and percentages are by weight.

EXAMPLE 1

Hydrolysis of Tetrahydrophthalic Anhydride to Tetrahydrophthalic Acid and Oxidation to 4,5-Dihydroxyhexahydrophthalic Acid To a 1000 mL flask equipped with stirrer and reflux condenser is charged 100 g of water. The contents of the flask are stirred while 182.4 g of tetrahydrophthalic anhydride is charged to the flask. Cooling water for the condenser is turned on and the contents of the flask are heated to 95°-100° C. and held at this temperature for 30 min. The resulting mixture, which corresponds to a solution of tetrahydrophthalic acid, is cooled to 80°-83° C., after which 165 g of 50% hydrogen peroxide is added over 10-20 min. and the temperature is maintained at 80°-83° for 3-4 h.

The course of the reaction is followed by HPLC using a Varian Chromatograph (Model 2510), with an ultraviolet detector (Model 2550 at 210 nm) and a Micropack MCH-5NCAP column. Phosphoric Acid (1.2%) is used as the mobile phase at a flow rate of 1 mL/min.

After 30 minutes' treatment with hydrogen peroxide at 80°-83° C., the tetrahydrophthalic acid is oxidized to 4,5-dihydroxyhexahydrophthalic acid (peak with a retention time of 3.27 min). The formation of 4,5-dihydroxyhexahydrophthalic acid is confirmed by comparing its retention time with that of a standard.

The peak at 1.38 min is hydrogen peroxide and that at 6.06 min is attributed to an intermediate. The broad peak about 68 min is unreacted tetrahydrophthalic acid.

Oxidation of tetrahydrophthalic acid to 4,5-dihydroxyhexahydophthalic acid is complete in 3-4 h. No peak, corresponding to butanetetracarboxylic acid is present in the HPLC chromatogram, run at the end of the reaction.

The identity of the product is confirmed by obtaining a $^{13}C$ NMR spectrum (in $D_2O$) and comparing it with the spectrum of a known sample.

EXAMPLE 2

Sodium Tungstate-catalyzed Oxidation of 4,5-Dihydroxyhexahydrophthalic Acid

Sodium tungstate catalyst (4.1 g in 20 mL of water) is added over 15 min to the solution obtained in Example 1. The reaction mixture is stirred at 80°-83° C. while 165 g of 50% hydrogen peroxide is added in ten portions at intervals of 60 min. After all the hydrogen peroxide is added, heating at 85°–90° C. and stirring is continued for 2 h more.

The course of the reaction is followed by HPLC, under conditions recited in Example 1. A chromatogram run shortly after addition of the catalyst and first additional portion of hydrogen peroxide shows a new peak at the retention time corresponding to that of butanetetracarboxylic acid. At the end of 9 h, following addition of the seventh portion of hydrogen peroxide, the major product on the chromatogram is that with a retention time of 4.03 min. In FIG. 1 is shown a chromatogram of the reaction mixture, at the end of the reaction. The major product (peak 8, retention time 3.88 min) is butanetetracarboxylic acid. The $^{13}$C NMR spectrum (in $D_2O$) is identical to that of a known sample of butanetetracarboxylic acid.

Peaks at 1.32 min, 3.30 min and 6.33 min in the chromatogram are attributed to hydrogen peroxide, glycol and an impurity, respectively.

Butanetetracarboxylic acid is isolated from the reaction mixture by conventional methods. The product is white. The yield is 82%, mp (capillary) 195°–196° C.

EXAMPLE 3

Phosphotungstic Acid-catalyzed Oxidation of 4,5-Dihydroxyhexahydrophthalic Acid

The reaction is carried out as in Example 2, using as catalyst 3 g of phosphotungstic acid in 20 mL of water. White butanetetracarboxylic acid is recovered from the reaction mixture by conventional techniques. The yield is 82%.

EXAMPLE 4

Sodium Tungstate-catalyzed Oxidation of 4,5-Dihydroxyhexahydrophthalic Acid

The oxidation is carried out as in Example 2, using 195 g of hydrogen peroxide and sodium tungstate dihydrate catalyst.

A comparative run, using the process of U.S. Pat. No. 4,833,272 (Example 5), and sodium tungsten dihydrate catalyst is made, starting with 182.4 g of tetrahydrophthalic anhydride and 195 g of 50% hydrogen peroxide and 4.1 g of catalyst. Hydrogen peroxide is added over 3 h.

The peak at 5.14/5.16 min in a chromatogram is attributed to an impurity and the peaks at 1.4 min and 2.8 min to hydrogen peroxide and glycol, respectively. The impurity peak is considerably larger in the product from the prior art process, than in the product from the process of the invention.

The yield of butanetetracarboxylic acid is 83%. The yield by the prior art process is 75%.

EXAMPLE 5

Phosphotungstic Acid-catalyzed Oxidation of 4,5-Dihydroxyhexahydrophthalic Acid

Oxidation of the glycol intermediate is carried out as in Example 3, except that 195 g of hydrogen peroxide is used.

A comparative run is done according to U.S. Pat. No. 4,833,272 (Example 5), adding hydrogen peroxide over 3 h, using 182 g of tetrahydrophthalic anhydride, 195 g of 50% hydrogen peroxide and 3 g of phosphotungstic acid [$H_3PO_4.12\ WO_3.xH_2O$].

The peak in a chromatogram at 5.81/5.85 min is attributed to an impurity and the peak at 1.4 min to hydrogen peroxide. The impurity peak is larger in the product from the prior art process than in the product from the process of the invention.

EXAMPLE 6

Manganese Chloride-catalyzed Oxidation of 4,5-Dihydroxyhexahydrophthalic Acid

Manganese (II) chloride (4 g in 20 mL of water) is used as catalyst for the oxidation of a product of Example 1. The course of the reaction is similar to that of Examples 2 and 3. The butanetetracarboxylic acid product, isolated using conventional procedures, is discolored. The yield is 43%.

EXAMPLE 7

Ferrous Sulfate-catalyzed Oxidation of 4,5-Dihydroxyhexahydrophthalic Acid

The oxidation is carried out as in Example 4, using as catalyst 4 g of ferrous sulfate in 20 mL of water. The product, after isolation by conventional methods, is discolored. The yield is 23%.

EXAMPLE 8

Hydrolysis and Oxidation of 3-Methyltetrahydrophthalic Anhydride

The Diels-Alder adduct from phthalic anhydride and piperylene is hydrolyzed and partially oxidized as in Example 1 and further oxidized as in Examples 1 and 2. Similar results are obtained.

EXAMPLE 9

Oxidation of 4,5-Dihydroxyhexahydrophthalic Acid 4,5-Dihydroxyhexahydrophthalic acid, prepared as in Example 1, is oxidized with hydrogen peroxide, using the following catalysts:
(a) $Na_2S_2O_8$
(b) $Na_2B_4O_7$
(c) $K_2Cr_2O_7$
(d) $Na_2SiO_3$
(e) $(NH_4)_2Ce(SO_4)_3.2H_2O$.
Similar results are obtained.

EXAMPLE 10

Hydrolysis of Tetrahydrophthalic Anhydride to Tetrahydrophthalic Acid and Oxidation to 4,5-Dihydroxyhexahydrophthalic Acid at 104°–110° C.

To a 1000-mL flask, equipped with stirrer, thermometer and reflux condenser is charged 91 g of water. The contents of the flask are stirred during the addition of 182.4 g of tetrahydrophthalic anhydride to the flask. Cooling water for the condenser is turned on and the contents of the flask are heated under reflux, at 104°–110° C., and held at this temperature for 5 min to convert tetrahydrophthalic anhydride to tetrahydrophthalic acid.

To the resulting solution of tetrahydrophthalic acid is added 90 g of 50% hydrogen peroxide solution over 10–20 min. The mixture in the flask is stirred and heated at 104°–110° C. under reflux for 90 min.

The course of the reaction is followed by HPLC using a Varian Chromatograph (Model 2510) with an ultraviolet detector (Model 2550 at 212 nm) and a micropack MCH-J-NCAP column. Phosphoric acid (1%) is used as the mobile phase at a flow rate of 1 mL/min. The identity of the peaks is confirmed using standards, obtained as in Example 1. A chromatogram at the end of 90 minutes' heating (FIG. 2) shows the complete oxidation of tetrahydrophthalic acid to 4,5-dihydroxyhexahydrophthalic acid. The peak at 2.84 min corresponds to 4,5-dihydroxytetrahydrophthalic acid. The peak at 1.40 min corresponds to hydrogen peroxide. Peaks at 3.94 min, 4.94 min and 5.60 min, respectively, are attributed to impurities. The absence of a peak at about 60 min demonstrates complete reaction of the tetrahydrophthalic acid. Minor variations in retention times are attributed to slight variations in flow rates or starting times.

The identity of the product is confirmed by comparison of a $^{13}C$ NMR spectrum (in $D_2O$) with that of a known sample.

EXAMPLE 11

Sodium Tungstate-catalyzed Oxidation of 4,5-Dihydroxyhexahydrophthalic Acid at 102°–110° C.

Sodium tungstate dihydrate ($Na_2WO_4.2 H_2O$) catalyst (3.0 g in 4 g of water) is added over 5 min to the solution, obtained in Example 10. The reaction mixture is stirred under reflux at 102°–110° C. while 270 g of 50% hydrogen peroxide solution is added over 3 h. After all of the hydrogen peroxide is added, stirring and heating at 102°–110° C. are continued for 3 h more.

Figure 3:
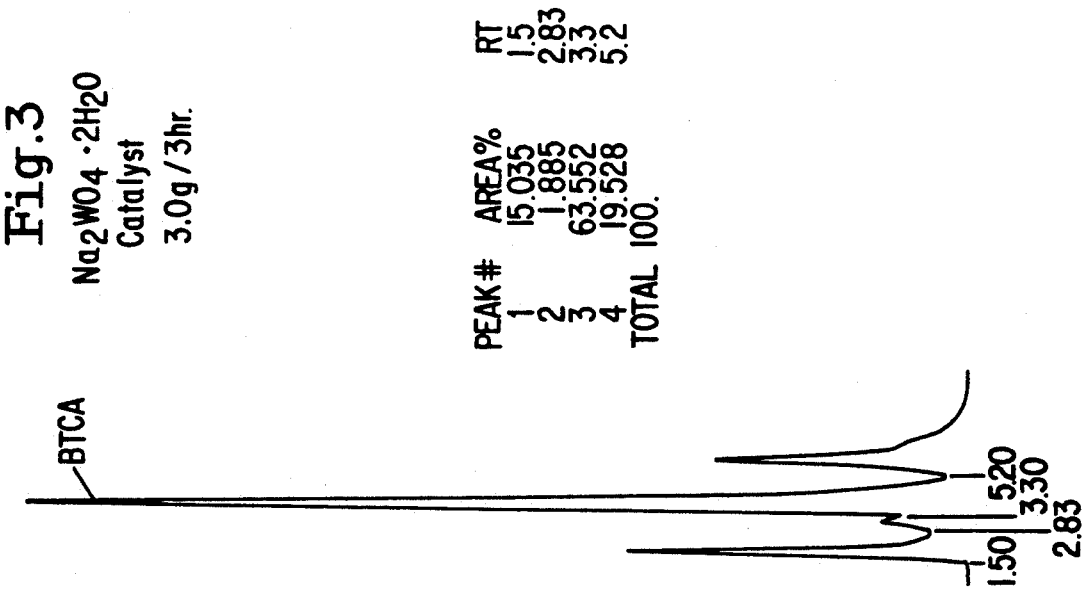

The course of the reaction is followed by HPLC as in Example 10. As shown in FIG. 3, the major product is 1,2,3,4-butanetetracarboxylic acid (peak at 3.3 min). The peak at 2.83 min is attributed to glycol and peaks at 1.50 and 5.20 min to impurities. The yield is 83%.

M.P. (capillary) 195°–196° C.

EXAMPLE 12

Phosphotungstic Acid-catalyzed Oxidation of 4,5-Dihydroxytetrahydrophthalic Acid at 102°–110° C.

The oxidation is carried out as in Example 11, using as catalyst 2.5 g of phosphotungstic acid in 4 mL of water. As shown in FIG. 4, the major product is butanetetracarboxylic acid. The white solid product is recovered from the reaction mixture by conventional techniques. The yield is 79%.

EXAMPLE 13

High-Temperature Oxidation of 4,5-Dihydroxyhexahydrophthalic Acid 4,5-Dihydroxyhexahydrophthalic acid, prepared as in Example 1 or 10, is oxidized with hydrogen peroxide as in Example 10, using the following catalysts:
(a) $Na_2S_2O_8$
(b) $Na_2B_4O_7$
(c) $K_2Cr_2O_7$
(d) $Na_2SiO_3$
(e) $(NH_4)_2Ce(SO_4)_3.2 H_2O$.
Similar results are obtained.

EXAMPLE 14

High-Temperature Oxidation of 3-Methyltetrahydrophthalic Anhydride

The Diels-Alder adduct from phthalic anhydride and piperylene is hydrolysed and partially oxidized as in Example 10 and further oxidized as in Example 11. Similar results are obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for oxidation of a tetrahydro compound of the formula

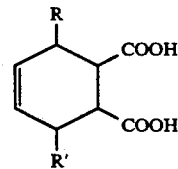

wherein R and R' independently are H, alkyl, aryl or halo, to a glycol of the formula

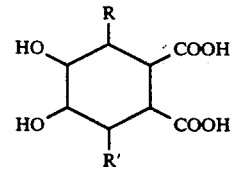

comprising treating the tetrahydro compound with hydrogen peroxide under reflux conditions at an elevated temperature above about 100° C. in the absence of a catalyst.

2. The process of claim 1, wherein R or R' is methyl.
3. The process of claim 1, wherein R and R' are H.
4. The process of claim 1, wherein hydrogen peroxide is in the form of an aqueous solution.
5. The process of claim 1, wherein oxidation is carried out with 1–2.6 moles of hydrogen peroxide per mole of tetrahydro compound.
6. The process of claim 1, wherein oxidation is carried out from about 100° C. to about 115° C.
7. The process of claim 1, wherein oxidation is carried out in the presence of 1.1–1.8 moles of hydrogen peroxide per mole of tetrahydro compound.
8. The process of claim 1, wherein R and R' are H; hydrogen peroxide is in the form of an aqueous solution and oxidation is carried out with 1.1–1.8 moles of hydrogen peroxide per mole of tetrahydro compound at 100°–110° C.
9. The process of claim 1, including further oxidation of the thus-formed glycol to a butanetetracarboxylic acid of the formula

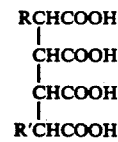

with hydrogen peroxide under reflux conditions at a temperature above about 50° C. in the presence of a catalyst selected from the group consisting of a manganese salt, an iron salt, a chromium salt, a cerium salt, a perborate, a persulfate, a silicate, tungstic acid or an ammonium or alkali metal salt or heteropolyacid thereof, or molybdic acid or an ammonium or alkali metal salt or heteropolyacid thereof.

10. The process of claim 9, carried out at a temperature above about 100° C.

11. The process of claim 9, wherein the catalyst is manganous chloride.

12. The process of claim 9, wherein the catalyst is ferrous sulfate.

13. The process of claim 9, wherein the catalyst is sodium tungstate.

14. The process of claim 9, wherein the catalyst is phosphotungstic acid.

15. The process of claim 9, wherein hydrogen peroxide is added incrementally or continuously to a reaction mixture containing glycol and catalyst.

16. The process of claim 9, carried out at a temperature of 100°–110° C.

17. The process of claim 9, wherein oxidation of the glycol is carried out with 3.0–4.5 moles of hydrogen peroxide per mole of glycol.

18. The process of claim 9, wherein oxidation of the glycol is carried out with 3.2–3.9 moles of hydrogen peroxide per mole of glycol.

19. The process of claim 9, wherein the catalyst is sodium tungstate, further oxidation is carried out at 100°–110° C., hydrogen peroxide is used in an amount of 3.2–3.9 moles per mole of glycol and hydrogen peroxide is added incrementally or continuously to a reaction mixture of catalyst and glycol.

20. The process of claim 9, wherein the catalyst is phosphotungstic acid, further oxidation is carried out at 100°–110° C., hydrogen peroxide is used in an amount of 3.2–3.9 moles per mole of glycol and hydrogen peroxide is added incrementally or continuously to a reaction mixture of catalyst and glycol.

21. A process for oxidation of a tetrahydro compound of the formula

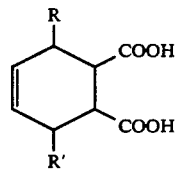

wherein R and R' independently are H, alkyl, aryl or halo, to a glycol of the formula

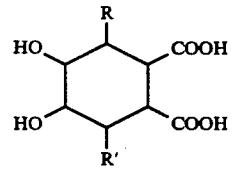

comprising treating the tetrahydro compound with hydrogen peroxide under reflux conditions at an elevated temperature from about 50° C. to about 100° C. in the absence of a catalyst and further oxidizing the thus-formed glycol to a butanetetracarboxylic acid of the formula

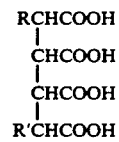

with hydrogen peroxide under reflux conditions at a temperature above about 100° C. in the presence of a catalyst selected from the group consisting of a manganese salt, an iron salt, a chromium salt, a cerium salt, a perborate, a persulfate, a silicate, tungstic acid or an ammonium or alkali metal salt or heteropolyacid thereof, or molybdic acid or an ammonium or alkali metal salt or heteropolyacid thereof.

* * * * *